US012746542B2

(12) United States Patent
Komai et al.

(10) Patent No.: US 12,746,542 B2

(45) Date of Patent: Sep. 29, 2026

(54) LEUKOCYTE CONCENTRATION SEPARATION DEVICE, BLOOD COLLECTION CONTAINER, AND METHOD FOR SEPARATING LEUKOCYTES

(71) Applicant: SEKISUI MEDICAL CO., LTD., Tokyo (JP)

(72) Inventors: Kuniya Komai, Yamaguchi (JP); Hironobu Isogawa, Yamaguchi (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 1065 days.

(21) Appl. No.: 17/908,407

(22) PCT Filed: Mar. 11, 2021

(86) PCT No.: PCT/JP2021/009804
§ 371 (c)(1),
(2) Date: Aug. 31, 2022

(87) PCT Pub. No.: WO2021/182575
PCT Pub. Date: Sep. 16, 2021

(65) Prior Publication Data

US 2023/0090675 A1 Mar. 23, 2023

(30) Foreign Application Priority Data

Mar. 11, 2020 (JP) ................................. 2020-042080

(51) Int. Cl.
*G01N 33/49* (2006.01)
*B01L 3/00* (2006.01)
*G01N 33/487* (2006.01)

(52) U.S. Cl.
CPC ........ *B01L 3/50215* (2013.01); *G01N 33/487* (2013.01); *B01L 2200/0631* (2013.01)

(58) Field of Classification Search
None
See application file for complete search history.

(56) References Cited

U.S. PATENT DOCUMENTS 4,416,777 A 11/1983 Kuroda et al.
4,487,700 A 12/1984 Kanter
(Continued)

FOREIGN PATENT DOCUMENTS

EP 0 844 482 5/1998
JP 54-238 1/1979
(Continued)

OTHER PUBLICATIONS

Office Action issued Nov. 19, 2024 in corresponding Canadian Patent Application No. 3,170,079.
(Continued)

*Primary Examiner* — Rebecca M Giere
(74) *Attorney, Agent, or Firm* — Wenderoth, Lind & Ponack, L.L.P.

(57) ABSTRACT

Provided is a blood collection container with which a specimen with a high leukocyte recovery rate and a small amount of contaminating erythrocytes can be obtained. A blood collection container according to the present invention is a blood collection container by which a predetermined amount of blood is collected, the blood collection container including:

a blood collection container main body; and
a hemocyte separation material contained in the blood collection container main body,
the hemocyte separation material having a specific gravity at 25 °C of 1.075 or more and 1.093 or less, and
the blood collection container including:
a configuration of including a hemagglutinating agent contained in the blood collection container main body (configuration A2); or (Continued)

a configuration of including an osmotic pressure regulator contained in the blood collection container main body, and when a water-soluble component contained in the blood collection container main body is dissolved with physiological saline in an amount equal to a predetermined amount of blood to be collected in the blood collection container to obtain a solution for osmotic pressure measurement, the solution for osmotic pressure measurement having an osmotic pressure of 300 mOsm/L or more and 500 mOsm/L or less (configuration B2).

12 Claims, 2 Drawing Sheets

(56) References Cited

U.S. PATENT DOCUMENTS

| | | | | |
|---|---|---|---|---|
| 4,640,785 | A | 2/1987 | Carroll et al. | |
| 4,751,001 | A | 6/1988 | Saunders | |
| 4,816,168 | A | 3/1989 | Carrol et al. | |
| 4,818,418 | A | 4/1989 | Saunders | |
| 5,397,479 | A | 3/1995 | Kass et al. | |
| 5,482,829 | A | 1/1996 | Kass et al. | |
| 5,702,884 | A | 12/1997 | Ekeze et al. | |
| 2006/0029923 | A1 | 2/2006 | Togawa et al. | |
| 2007/0082370 | A1 | 4/2007 | Togawa et al. | |
| 2007/0105156 | A1 | 5/2007 | Togawa et al. | |
| 2010/0133181 | A1 | 6/2010 | Wood et al. | |
| 2010/0151438 | A1 | 6/2010 | Yu et al. | |
| 2012/0275955 | A1* | 11/2012 | Haghgooie ...... | A61B 5/150099 210/321.62 |
| 2013/0045852 | A1 | 2/2013 | Chapman et al. | |
| 2015/0093739 | A1 | 4/2015 | Wood et al. | |
| 2015/0148212 | A1 | 5/2015 | Chiyoda et al. | |
| 2015/0299657 | A1 | 10/2015 | McCloskey et al. | |
| 2016/0252434 | A1 | 9/2016 | Smith et al. | |
| 2017/0131189 | A1* | 5/2017 | Sugimoto ................ | G01N 1/20 |
| 2017/0153223 | A1 | 6/2017 | Karp et al. | |
| 2018/0120295 | A1 | 5/2018 | Sitar | |
| 2018/0195938 | A1 | 7/2018 | Lee | |
| 2018/0292298 | A1 | 10/2018 | Smith et al. | |
| 2018/0303395 | A1* | 10/2018 | Tan ..................... | A61M 1/3496 |
| 2019/0162716 | A1 | 5/2019 | Mikhaiel et al. | |
| 2019/0226952 | A1 | 7/2019 | Muramatsu et al. | |
| 2020/0209215 | A1 | 7/2020 | Okamoto et al. | |
| 2021/0088503 | A1 | 3/2021 | Karp et al. | |

FOREIGN PATENT DOCUMENTS

| | | | |
|---|---|---|---|
| JP | 57-37259 | | 3/1982 |
| JP | 57-54860 | | 4/1982 |
| JP | 58-54130 | | 12/1983 |
| JP | 60-3367 | | 1/1985 |
| JP | 61-84557 | A | 4/1986 |
| JP | 4-42627 | | 7/1992 |
| JP | 4-65981 | | 10/1992 |
| JP | 5-322886 | | 12/1993 |
| JP | 8-510322 | | 10/1996 |
| JP | 10-2898 | | 1/1998 |
| JP | 10-160731 | | 6/1998 |
| JP | 2004-3920 | | 1/2004 |
| JP | 2004-344874 | | 12/2004 |
| JP | 2017-102114 | | 6/2017 |
| JP | 2017-129429 | | 7/2017 |
| JP | 2017-523385 | | 8/2017 |
| JP | 2018-29791 | | 4/2018 |
| WO | 94/25135 | | 11/1994 |
| WO | 2010/132783 | | 11/2010 |
| WO | 2013/168767 | | 11/2013 |
| WO | 2015/158683 | | 10/2015 |
| WO | 2019/131613 | | 7/2019 |

OTHER PUBLICATIONS

Office Action issued Nov. 26, 2025 in corresponding European Patent Application No. 21767156.9.
International Preliminary Report on Patentability and Written Opinion issued Sep. 6, 2022 in corresponding International (PCT) Patent Application No. PCT/JP2021/009804.
Office Action dated Jan. 25, 2024 in corresponding Canadian Patent Application No. 3,170,079.
Extended European Search Report issued Mar. 7, 2024 in corresponding European Patent Application No. 21767156.9.
International Search Report issued May 25, 2021 in International (PCT) Application No. PCT/JP2021/009804.

* cited by examiner

[FIG. 1.]
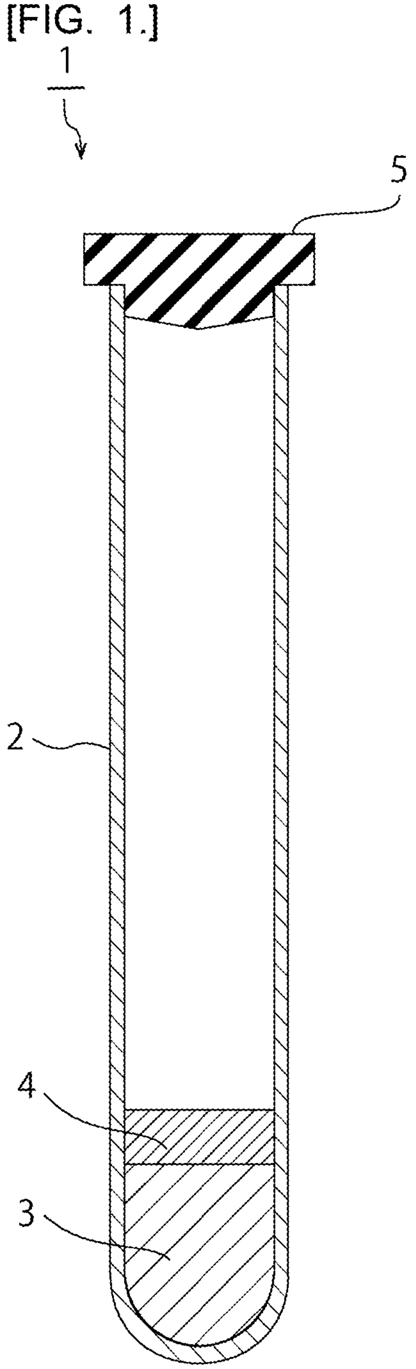

[FIG. 2.]
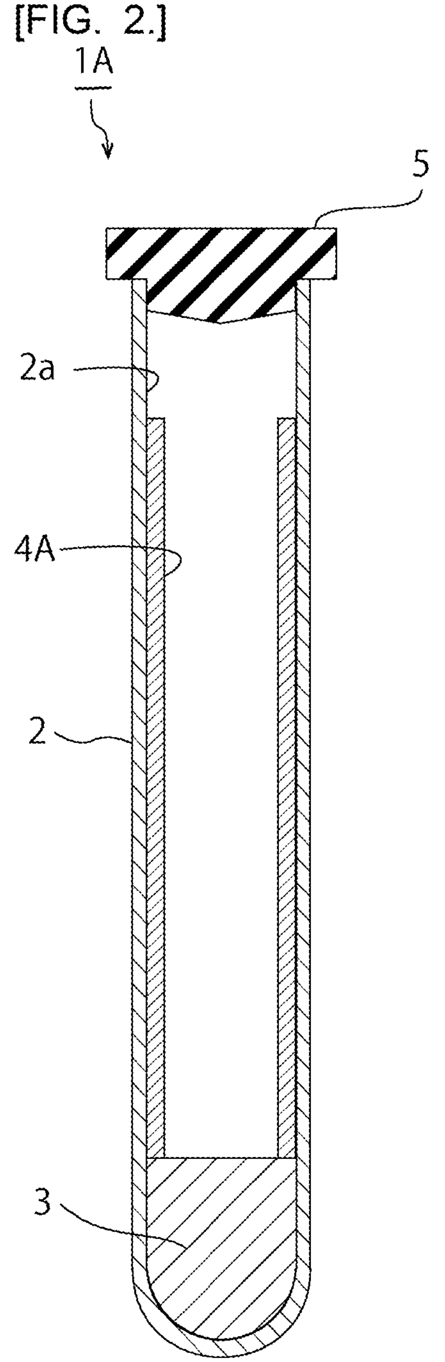

LEUKOCYTE CONCENTRATION SEPARATION DEVICE, BLOOD COLLECTION CONTAINER, AND METHOD FOR SEPARATING LEUKOCYTES

TECHNICAL FIELD

The present invention relates to a leukocyte concentration separation device for concentrating and separating leukocytes present in a blood-derived sample. The present invention also relates to a blood collection container capable of concentrating and separating leukocytes. The present invention also relates to a method for separating leukocytes using the leukocyte separation device or the blood collection container described above.

BACKGROUND ART

In clinical examination, specific cells are concentrated and separated from blood, and examination using the separated cells is performed. For example, in order to observe the form of leukocytes, analyze surface antigens of leukocytes, and examine chromosomes and genes inside leukocytes, erythrocytes are removed from blood, and leukocytes are separated.

As a method for removing erythrocytes from blood and recovering leukocytes, a hemolysis method and a centrifugation method using ficoll are known, but these methods are complicated in operation, and the leukocyte recovery rate greatly varies depending on the skill of an operator.

Devices capable of easily separating leukocytes regardless of the skill of an operator are described in the following Patent Documents 1 and 2.

Patent Document 1 below describes a blood collection container containing a gel composition having a particular specific gravity. Blood is collected in the blood collection container and centrifuged, whereby erythrocytes settle on the lower side of the gel composition due to the difference in specific gravity, and leukocytes are concentrated and separated on the upper side of the gel composition.

Patent Document 2 below describes a blood collection container containing a gel composition having a particular specific gravity and a water-soluble density gradient substance having a specific gravity larger than that of the gel composition. Blood is collected in the blood collection container and centrifuged, whereby erythrocytes settle on the lower side of the gel composition due to the difference in specific gravity, and leukocytes are concentrated and separated in a layer formed between the gel composition and a plasma layer.

RELATED ART DOCUMENT

Patent Documents

Patent Document 1: WO 2019/131613 A1
Patent Document 2: JP S61-084557 A

SUMMARY OF THE INVENTION

Problems to be Solved by the Invention

In the method described in Patent Document 1, the amount of erythrocytes contaminating in a layer of leukocytes deposited in the upper part of the gel composition after centrifugation may increase. When examination on leukocytes is performed using a specimen with a large amount of contaminating erythrocytes, there is a possibility that the examination accuracy decreases and a normal examination result cannot be obtained.

In addition, in the method described in Patent Document 2, although the amount of erythrocytes contaminating in the layer of leukocytes can be reduced to some extent, it is difficult to increase the leukocyte recovery rate. When a specimen with a smaller amount of recovered leukocytes is used, there is also a possibility that the examination accuracy decreases and a normal examination result cannot be obtained.

It is an object of the present invention to provide a leukocyte concentration separation device and a blood collection container capable of obtaining a specimen with a high leukocyte recovery rate and a small amount of contaminating erythrocytes. It is also an object of the present invention to provide a method for separating leukocytes using the leukocyte concentration separation device or the blood collection container described above.

Means for Solving the Problem

According to a broad aspect of the present invention, there is provided a leukocyte concentration separation device into which a predetermined amount of a blood-derived sample is added, the leukocyte concentration separation device being intended to concentrate and separate leukocytes present in the blood-derived sample, the leukocyte concentration separation device including:

a container main body; and a hemocyte separation material contained in the container main body, the hemocyte separation material having a specific gravity at 25 °C of 1.075 or more and 1.093 or less, and the leukocyte concentration separation device including a configuration A1 or a configuration B1 below.

A configuration A1: the leukocyte concentration separation device including a hemagglutinating agent contained in the container main body.

A configuration B1: the leukocyte concentration separation device including an osmotic pressure regulator contained in the container main body, and when a water-soluble component contained in the container main body is dissolved with physiological saline in an amount equal to the predetermined amount of a blood-derived sample to be added into the leukocyte concentration separation device to obtain a solution for osmotic pressure measurement, the solution for osmotic pressure measurement having an osmotic pressure of 300 mOsm/L or more and 500 mOsm/L or less.

According to a broad aspect of the present invention, there is provided a blood collection container by which a predetermined amount of blood is collected, the blood collection container including:

a blood collection container main body; and a hemocyte separation material contained in the blood collection container main body, the hemocyte separation material having a specific gravity at 25 °C of 1.075 or more and 1.093 or less, and the blood collection container including a configuration A2 or a configuration B2 below.

A configuration A2: the blood collection container including a hemagglutinating agent contained in the blood collection container main body.

A configuration B2: the blood collection container including an osmotic pressure regulator contained in the blood collection container main body, and when a water-soluble component contained in the blood collection container main body is dissolved with physiological saline in an amount equal to the predetermined amount of blood to be collected in the blood collection container to obtain a solution for osmotic pressure measurement is obtained, the solution for osmotic pressure measurement having an osmotic pressure of 300 mOsm/L or more and 500 mOsm/L or less.

In a specific aspect of the blood collection container according to the present invention, the hemocyte separation material is a hemocyte separation composition having thixotropy.

In a specific aspect of the blood collection container according to the present invention, the blood collection container includes the configuration A2.

In a specific aspect of the blood collection container according to the present invention, the hemagglutinating agent is dextran, hydroxyethyl starch, or polyethylene glycol.

In a specific aspect of the blood collection container according to the present invention, the dextran has a weight average molecular weight of 50,000 or more.

In a specific aspect of the blood collection container according to the present invention, the blood collection container includes the configuration B2.

In a specific aspect of the blood collection container according to the present invention, the solution for osmotic pressure measurement has an osmotic pressure of 320 mOsm/L or more and 360 mOsm/L or less.

In a specific aspect of the blood collection container according to the present invention, the hemocyte separation material has a specific gravity at 25 °C of 1.082 or more and 1.090 or less, and the solution for osmotic pressure measurement has an osmotic pressure of 320 mOsm/L or more and 360 mOsm/L or less.

In a specific aspect of the blood collection container according to the present invention, the osmotic pressure regulator is sodium chloride or glucose.

In a specific aspect of the blood collection container according to the present invention, the blood collection container includes the configuration A2 and the configuration B2.

In a specific aspect of the blood collection container according to the present invention, the blood collection container includes an anticoagulant contained in the blood collection container main body.

In a specific aspect of the blood collection container according to the present invention, the blood collection container includes an antioxidant contained in the blood collection container main body.

In a specific aspect of the blood collection container according to the present invention, the antioxidant is ascorbic acid or an inorganic salt of ascorbic acid.

According to a broad aspect of the present invention, there is provided a method for separating leukocytes using the above-described leukocyte concentration separation device, the method including the steps of:

adding a blood-derived sample into the leukocyte concentration separation device; and centrifuging the leukocyte concentration separation device into which the blood-derived sample has been added.

According to a broad aspect of the present invention, there is provided a method for separating leukocytes using the above-described blood collection container, the method including the steps of:

collecting blood in the blood collection container; and centrifuging the blood collection container by which the blood has been collected.

According to a broad aspect of the present invention, there is provided a leukocyte concentration separation system in which a predetermined amount of a blood-derived sample is collected, the leukocyte concentration separation system being intended to concentrate and separate leukocytes present in the blood-derived sample, the leukocyte concentration separation system including a hemocyte separation material having a specific gravity at 25 °C of 1.075 or more and 1.093 or less, and the leukocyte concentration separation system including a configuration A3 or a configuration B3 below.

A configuration A3: the leukocyte concentration separation system including a hemagglutinating agent.

A configuration B3: the leukocyte concentration separation system including an osmotic pressure regulator, and when a water-soluble component to be mixed with the blood-derived sample is dissolved with physiological saline in an amount equal to the predetermined amount of the blood-derived sample to obtain a solution for osmotic pressure measurement, the solution for osmotic pressure measurement having an osmotic pressure of 300 mOsm/L or more and 500 mOsm/L or less.

Effect of the Invention

A leukocyte concentration separation device according to the present invention is a leukocyte concentration separation device into which a predetermined amount of a blood-derived sample is added, the leukocyte concentration separation device being intended to concentrate and separate leukocytes present in the blood-derived sample, the leukocyte concentration separation device including:

a container main body; and a hemocyte separation material contained in the container main body, the hemocyte separation material having a specific gravity at 25 °C of 1.075 or more and 1.093 or less, and the leukocyte concentration separation device including a configuration A1 or a configuration B1 below:

a configuration A1: the leukocyte concentration separation device including a hemagglutinating agent contained in the container main body; or a configuration B1: the leukocyte concentration separation device including an osmotic pressure regulator contained in the container main body, and when a water-soluble component contained in the container main body is dissolved with physiological saline in an amount equal to the predetermined amount of a blood-derived sample to be added to the leukocyte concentration separation device to obtain a solution for osmotic pressure measurement, the solution for osmotic pressure measurement having an osmotic pressure of 300 mOsm/L or more and 500 mOsm/L or less.

The leukocyte concentration separation device according to the present invention, having the above-described configuration, is capable of obtaining a specimen with a high leukocyte recovery rate and a small amount of contaminating erythrocytes.

A blood collection container according to the present invention is a blood collection container by which a predetermined amount of blood is collected, the blood collection container including:

a blood collection container main body; and a hemocyte separation material contained in the blood collection container main body, the hemocyte separation material having a specific gravity at 25 °C of 1.075 or more and 1.093 or less, and the blood collection container including a configuration A2 or a configuration B2 below:

a configuration A2: the blood collection container including a hemagglutinating agent contained in the blood collection container main body; or a configuration B2: the blood collection container including an osmotic pressure regulator contained in the blood collection container main body, and when a water-soluble component contained in the blood collection container main body is dissolved with physiological saline in an amount equal to a predetermined amount of blood to be collected in the blood collection container to obtain a solution for osmotic pressure measurement, the solution for osmotic pressure measurement having an osmotic pressure of 300 mOsm/L or more and 500 mOsm/L or less. The blood collection container according to the present invention, having the above-described configuration, is capable of obtaining a specimen with a high leukocyte recovery rate and a small amount of contaminating erythrocytes.

BRIEF DESCRIPTION OF DRAWINGS

FIG. 1 is a front cross-sectional view of a blood collection container according to a first embodiment of the present invention.

FIG. 2 is a front cross-sectional view of a blood collection container according to a second embodiment of the present invention.

MODE(S) FOR CARRYING OUT THE INVENTION

Hereinafter, the present invention will be described in detail.

A leukocyte concentration separation device according to the present invention is a leukocyte concentration separation device into which a predetermined amount of a blood-derived sample is added, the leukocyte concentration separation device being intended to concentrate and separate leukocytes present in the blood-derived sample, the leukocyte concentration separation device including:

a container main body; and a hemocyte separation material contained in the container main body, the hemocyte separation material having a specific gravity at 25 °C of 1.075 or more and 1.093 or less, and the leukocyte concentration separation device including a configuration A1 or a configuration B1 below.

A configuration A1: the leukocyte concentration separation device including a hemagglutinating agent contained in the container main body.

A configuration B1: the leukocyte concentration separation device including an osmotic pressure regulator contained in the container main body, and when a water-soluble component contained in the container main body is dissolved with physiological saline in an amount equal to the predetermined amount of a blood-derived sample to be added to the leukocyte concentration separation device to obtain a solution for osmotic pressure measurement, the solution for osmotic pressure measurement having an osmotic pressure of 300 mOsm/L or more and 500 mOsm/L or less.

A blood collection container according to the present invention is a blood collection container by which a predetermined amount of blood is collected, the blood collection container including:

a blood collection container main body; and a hemocyte separation material contained in the blood collection container main body, the hemocyte separation material having a specific gravity at 25 °C of 1.075 or more and 1.093 or less, and the blood collection container including a configuration A2 or a configuration B2 below.

A configuration A2: the blood collection container including a hemagglutinating agent contained in the blood collection container main body.

A configuration B2: the blood collection container including an osmotic pressure regulator contained in the blood collection container main body, and when a water-soluble component contained in the blood collection container main body is dissolved with physiological saline in an amount equal to a predetermined amount of blood to be collected in the blood collection container to obtain a solution for osmotic pressure measurement, the solution for osmotic pressure measurement having an osmotic pressure of 300 mOsm/L or more and 500 mOsm/L or less.

In the case of the leukocyte concentration separation device according to the present invention as well as in the case of the blood collection container according to the present invention, with the above-described configuration, it is possible to obtain a specimen with a high leukocyte recovery rate and a small amount of contaminating erythrocytes. In the case of the leukocyte concentration separation device according to the present invention as well as in the case of the blood collection container according to the present invention, with the above-described configuration, it is possible to obtain a specimen with a high content of leukocytes and a low content of erythrocytes.

The leukocyte concentration separation device according to the present invention may include the configuration A1, or may include the configuration B1, or may include both of the configurations A1 and B1. From the viewpoint of more effectively exhibiting the effects of the present invention, the leukocyte concentration separation device according to the present invention preferably includes both of the configuration A1 and the configuration B1.

The blood collection container according to the present invention may include the configuration A2, or may include the configuration B2, or may include both of the configurations A2 and B2. From the viewpoint of more effectively exhibiting the effects of the present invention, the blood collection container according to the present invention preferably includes both of the configuration A2 and the configuration B2.

When the blood collection container according to the present invention includes the configuration A2, agglutination of erythrocytes is caused by a hemagglutinating agent. Subjecting the blood collection container to centrifugation causes agglutinated erythrocytes to move satisfactorily downward to below a hemocyte separation material having a particular specific gravity. This also causes leukocytes to move satisfactorily upward to above the hemocyte separation material having a particular specific gravity. As a result, a specimen with a high leukocyte recovery rate and a small amount of contaminating erythrocytes can be obtained.

When the blood collection container according to the present invention includes the configuration B2, the blood, collected in the blood collection container, has a greater osmotic pressure. Therefore, the moisture in the leukocytes and the moisture in the erythrocytes move to the outside of the hemocytes, and the specific gravities of the leukocytes and the erythrocyte increase. As a result, the difference between the specific gravity of the leukocytes and the specific gravity of the erythrocytes can be increased. Subjecting the blood collection container to centrifugation causes the erythrocytes having a greater specific gravity to move satisfactorily downward to below a hemocyte separation material having a particular specific gravity. This also causes leukocytes to move satisfactorily upward to above the hemocyte separation material having a particular specific gravity. As a result, a specimen with a high leukocyte recovery rate and a small amount of contaminating erythrocytes can be obtained.

With the leukocyte concentration separation device according to the present invention, having a configuration similar to the above-described configuration, it is also possible to obtain a specimen with a high leukocyte recovery rate and a small amount of contaminating erythrocytes.

When the leukocyte concentration separation device according to the present invention includes both of the configurations A1 and B1, and when the blood collection container according to the present invention includes both of the configurations A2 and B2, the effect by the agglutination of the erythrocytes and the effect by the specific gravity are achieved together, whereby the effects of the present invention are exhibited more effectively.

In the leukocyte concentration separation device including the above configuration B1, when a water-soluble component contained in the container main body is dissolved in physiological saline in an amount equal to a predetermined amount of a blood-derived sample added into the leukocyte concentration separation device to obtain a solution for osmotic pressure measurement, the obtained solution for osmotic pressure measurement has an osmotic pressure of 300 mOsm/L or more and 500 mOsm/L or less.

In the blood collection container including the above configuration B2, when a water-soluble component contained in the blood collection container main body is dissolved in physiological saline in an amount equal to a predetermined amount of blood collected in the blood collection container to obtain a solution for osmotic pressure measurement, the obtained solution for osmotic pressure measurement has an osmotic pressure of 300 mOsm/L or more and 500 mOsm/L or less.

The solution for osmotic pressure measurement is prepared specifically in the following manner.

An amount of physiological saline in an amount equal to a predetermined amount of a blood-derived sample added into the leukocyte concentration separation device or a predetermined amount of blood collected in the blood collection container is added into the leukocyte concentration separation device or the blood collection container. For example, in a blood collection container by which 5 mL of blood is collected, 5 mL of physiological saline is added into the blood collection container. After the addition, the resultant is mixed by inversion so that the water-soluble component is dissolved with physiological saline, whereby a solution for osmotic pressure measurement can be obtained. Examples of the water-soluble component include an osmotic pressure regulator, a hemagglutinating agent, and a liquid containing them.

The osmotic pressure of the solution for osmotic pressure measurement is measured by the freezing point depressing method using an osmosis meter (for example, "OM-6060" manufactured by ARKRAY Inc.).

The osmotic pressure of the solution for osmotic pressure measurement is preferably 300 mOsm/L or more, more preferably 310 mOsm/L or more, still more preferably 320 mOsm/L or more, and preferably 500 mOsm/L or less, more preferably 400 mOsm/L or less, still more preferably 360 mOsm/L or less. When the osmotic pressure is at or above the lower limit, contamination of erythrocytes in a specimen can be more effectively suppressed. When the hemocyte separation material has a specific gravity at 25 °C of 1.082 or more and 1.090 or less, and the solution for osmotic pressure measurement has an osmotic pressure of 320 mOsm/L or more and 360 mOsm/L or less, the effects of the present invention are more effectively exhibited.

(Hemocyte Separation Material)

The leukocyte concentration separation device includes a hemocyte separation material contained in the container main body. The blood collection container includes a hemocyte separation material contained in the blood collection container main body. The hemocyte separation material has a specific gravity at 25 °C of 1.075 or more and 1.093 or less. Examples of the hemocyte separation material include a hemocyte separation composition and a hemocyte separation jig. The hemocyte separation material is preferably the hemocyte separation composition because such a hemocyte separation composition can be easily produced.

The location where the hemocyte separation material is stored is not particularly limited as long as it is in the container main body or the blood collection container main body. In the leukocyte concentration separation device, the hemocyte separation material may be disposed at a bottom portion in the container main body or may be disposed on an inner wall surface thereof. In the blood collection container, the hemocyte separation material may be disposed at a bottom portion in the blood collection container main body or may be disposed on an inner wall surface thereof.

<Hemocyte Separation Composition>

The hemocyte separation composition is a composition that moves to between leukocytes and erythrocytes during centrifugation to form a partition. In addition, the hemocyte separation composition is used for the purpose of preventing erythrocytes from contaminating in a layer of leukocytes after centrifugation. The hemocyte separation composition preferably has thixotropy, and more preferably is a gel composition having thixotropy. In the leukocyte concentration separation device, the hemocyte separation composition may be contained in a bottom portion in the container main body or may be disposed on an inner wall surface thereof. From the viewpoint of more effectively exhibiting the effects of the present invention, it is preferable that the hemocyte separation composition is contained in the bottom portion of the container main body. In the blood collection container, the hemocyte separation composition may be contained in a bottom portion in the blood collection container main body or may be disposed on an inner wall surface thereof. From the viewpoint of more effectively exhibiting the effects of the present invention, it is preferable that the hemocyte separation composition is contained in the bottom portion of the blood collection container main body.

The hemocyte separation composition preferably contains an organic component having fluidity at 25 °C and an inorganic fine powder. One kind of the organic component having fluidity at 25 °C may be used alone, and two or more kinds of the same may be used in combination. So may be the inorganic fine powder.

Organic Component Having Fluidity at 25 °C:

The phrase "having fluidity at 25 °C" means that the viscosity at 25 °C is 500 Pa·s or less.

The viscosity of the organic component at 25 °C is preferably 30 Pa·s or more, more preferably 50 Pa·s or more, and preferably 200 Pa·s or less, more preferably 100 Pa·s or less. When the viscosity is at or above the lower limit and at or below the upper limit, the fluidity of the hemocyte separation composition is enhanced, and the strength of the partition can be enhanced.

The viscosity of the organic component at 25 °C is measured using an E-type viscometer (For example, "TVE-35" manufactured by Toki Sangyo Co., Ltd.) under the conditions of 25 °C and a shear rate of 1.0 $sec^{-1}$.

Examples of the organic component include a resin, and a mixture of a resin and an organic compound such as a plasticizer. When the organic component is a mixture of the resin and the organic compound, the resin or the organic compound may not have fluidity as long as the mixture (organic component) has fluidity. When the organic component is a mixture of the resin and the organic compound, the resin may be, for example, a resin that is solid at 25 °C. One kind of the resin may be used alone, or two or more kinds of the same may be used in combination. So may be the organic compound.

Examples of the resin include a petroleum resin, a cyclopentadiene resin, a polyester resin, a polyurethane resin, a (meth)acrylic resin, a silicone resin, an α-olefin-fumaric acid ester copolymer, a copolymer of sebacic acid, 2,2-dimethyl-1,3-propanediol, and 1,2-propanediol, a polyether polyurethane resin, and a polyether polyester resin. One kind of the resin may be used alone, or two or more kinds of the same may be used in combination.

Examples of commercially available products of the petroleum resin include "Regalite S5090" manufactured by Eastman Chemical Company.

Examples of the cyclopentadiene resin include a polymer of a cyclopentadiene monomer, a copolymer of a cyclopentadiene monomer and an aromatic monomer, and a dicyclopentadiene resin. The cyclopentadiene resin may be hydrogenated. The polymer of the cyclopentadiene monomer and the copolymer of the cyclopentadiene monomer and the aromatic monomer may be oligomers.

Examples of the cyclopentadiene monomer include cyclopentadiene, dicyclopentadiene, and an alkyl-substituted derivative of cyclopentadiene.

Examples of the aromatic monomer include styrene, methylstyrene, indene, and methylindene.

Examples of a commercially available product of the dicyclopentadiene resin include "SCOREZ SU-500" and "SCOREZ SU-90" manufactured by KOLON Industries, Inc.

Examples of the polyester resin include a polyalkylene terephthalate resin and a polyalkylene naphthalate resin. Examples of the polyalkylene terephthalate resin include polyethylene terephthalate, polybutylene terephthalate, and poly-1,4-cyclohexanedimethylene terephthalate.

Examples of the polyurethane resin include a reaction product of a polyol compound and an isocyanate compound.

Examples of the (meth)acrylic resin include a resin obtained by polymerizing at least one (meth)acrylic acid ester monomer, and a resin obtained by polymerizing at least one (meth)acrylic acid ester monomer and at least one monomer other than the (meth)acrylic acid ester monomer.

Examples of the (meth)acrylic acid ester monomer include (meth)acrylic acid alkyl ester having an alkyl group containing 1 to 20 carbon atoms, (meth)acrylic acid polyalkylene glycol ester, (meth)acrylic acid alkoxyalkyl ester, (meth)acrylic acid hydroxyalkyl ester, (meth)acrylic acid glycidyl ester, (meth)acrylic acid dialkylaminoalkyl ester, (meth)acrylic acid benzyl ester, (meth)acrylic acid phenoxyalkyl ester, (meth)acrylic acid cyclohexyl ester, (meth) acrylic acid isobornyl ester, and (meth)acrylic acid alkoxysilyl alkyl ester. One kind of the (meth)acrylic acid ester monomer may be used alone, or two or more kinds of the same may be used in combination.

Examples of the organic compound include a benzene polycarboxylic acid alkyl ester derivative. The organic compound is preferably a benzene polycarboxylic acid alkyl ester derivative. Therefore, the organic component is preferably a mixture of the resin and the benzene polycarboxylic acid alkyl ester derivative.

Examples of the benzene polycarboxylic acid alkyl ester derivative include a phthalic acid ester, a trimellitic acid ester, and a pyromellitic acid ester. One kind of the benzene polycarboxylic acid alkyl ester derivative may be used alone, or two or more kinds of the same may be used in combination.

Examples of the trimellitic acid ester include tri-n-octyl trimellitate, triisooctyl trimellitate, and triisodecyl trimellitate.

Examples of the pyromellitic acid ester include tetraisooctyl pyromellitate.

Examples of the commercially available product of the trimellitic acid ester include "Monocizer W-700" and "Monocizer W-750" manufactured by DIC Corporation, and "SANSO CIZER TOTM" and "SANSO CIZER TITM" manufactured by New Japan Chemical Co., Ltd.

Examples of the commercially available product of the pyromellitic acid ester include "Monocizer W-7010" manufactured by DIC Corporation.

The benzene polycarboxylic acid alkyl ester derivative is preferably a phthalic acid ester, a trimellitic acid ester, or a pyromellitic acid ester, and more preferably a trimellitic acid ester.

The content of the organic component in 100 wt % of the hemocyte separation composition is preferably 80 wt % or more, more preferably 85 wt % or more, and still more preferably 90 wt % or more, as well as preferably 95 wt % or less.

Inorganic Fine Powder:

Examples of the inorganic fine powder include fine powder silica, titanium oxide powder, zinc oxide powder, calcium carbonate powder, alumina powder, glass fine powder, talc powder, kaolin powder, bentonite powder, titania powder, and zirconium powder.

The inorganic fine powder more preferably contains fine powder silica and an inorganic fine powder different from the fine powder silica. The inorganic fine powder different from the fine powder silica is preferably an inorganic fine powder having a specific gravity larger than that of the fine powder silica, and more preferably an inorganic fine powder having a specific gravity of 3 or more, such as a zinc oxide powder, a titanium oxide powder, or an alumina powder.

From the viewpoint of more effectively exhibiting the effects of the present invention, the inorganic fine powder preferably contains fine powder silica.

Examples of the fine powder silica include natural silica and synthetic silica. Examples of the synthetic silica include hydrophilic silica and hydrophobic silica. Hydrophilic silica has an action of imparting thixotropy to the hemocyte separation composition and adjusting the specific gravity by hydrogen bonding between hydroxyl groups on the particle surfaces. On the other hand, hydrophobic silica has a smaller thixotropy imparting effect than hydrophilic silica.

From the viewpoint of maintaining both the specific gravity and the thixotropy of the hemocyte separation composition in suitable ranges, the fine powder silica preferably contains hydrophilic silica, and more preferably contains hydrophilic silica and hydrophobic silica. The fine powder silica preferably contains at least hydrophilic silica.

The content of the hydrophilic silica in 100 wt % of the hemocyte separation composition is preferably 0.01 wt % or more, more preferably 0.1 wt % or more, and still more preferably 0.3 wt % or more, as well as preferably 2.50 wt % or less, and more preferably 2.00 wt % or less. When the content of the hydrophilic silica is at or above the lower limit and at or below the upper limit, both the specific gravity and the thixotropy of the hemocyte separation composition can be maintained in a more suitable range.

The content of the fine powder silica in 100 wt % of the hemocyte separation composition is preferably 0.1 wt % or more, more preferably 1 wt % or more, and still more preferably 3 wt % or more, as well as preferably 10 wt % or less, and more preferably 5 wt % or less. When the content of the fine powder silica is at or above the lower limit and at or below the upper limit, both the specific gravity and the thixotropy of the hemocyte separation composition can be maintained in a more suitable range.

The average particle diameters of the fine powder silica and the inorganic fine powder different from the fine powder silica are not particularly limited. The average particle diameter of the fine powder silica may be 1 nm or more, or 10 nm or more, as well as 500 nm or less, or 100 nm or less. The average particle diameter of the inorganic fine powder different from the fine powder silica is not particularly limited. The average particle diameter of the inorganic fine powder may be 10 nm or more, or 100 nm or more, as well as 10 μm or less, or 1 μm or less.

The average particle diameters of the fine powder silica and the inorganic fine powder different from the fine powder silica are average diameters measured on a volume basis, and are values of median diameters (D50) corresponding to 50%. The volume average particle diameter (D50) can be measured by the laser diffraction/scattering method, the image analysis method, the Coulter method, the centrifugal sedimentation method, or the like. The volume average particle diameter (D50) is preferably determined by the measurement by the laser diffraction/scattering method or the image analysis method.

The content of the inorganic fine powder in 100 wt % of the hemocyte separation composition is preferably 0.1 wt % or more, more preferably 1 wt % or more, and still more preferably 3 wt % or more, as well as preferably 10 wt % or less, and more preferably 5 wt % or less. When the content of the inorganic fine powder is at or above the lower limit and at or below the upper limit, both the specific gravity and the thixotropy of the hemocyte separation composition can be maintained in a more suitable range.

Other Components:

The hemocyte separation composition may contain components other than the above-described components as long as the effects of the present invention are not impaired. The hemocyte separation composition may contain, for example, an organic gelling agent, a thermoplastic elastomer, a polyalkylene glycol, a silicone oil, an auxiliary solvent, an antioxidant, a colorant, water, and the like as the other components. One kind of the other component may be used alone, or two or more kinds of the same may be used in combination.

Other Details:

The hemocyte separation composition has a specific gravity at 25 °C of 1.075 or more and 1.093 or less. The specific gravity at 25 °C of the hemocyte separation composition is preferably 1.077 or more, and more preferably 1.082 or more, as well as 1.090 or less, and more preferably 1.088 or less. When the specific gravity is at or above the lower limit and at or below the upper limit, it is possible to satisfactorily obtain a specimen in which the leukocyte recovery rate is still higher and the amount of contaminating erythrocytes is still smaller.

The specific gravity at 25 °C of the hemocyte separation composition is measured as follows: drops of the hemocyte separation composition are dropped one by one sequentially into saline at 25 °C whose specific gravity is adjusted stepwise at intervals of 0.002, and determination is made based on rise and fall of each drop in saline.

The viscosity at 25 °C of the hemocyte separation composition is preferably 100 Pa·s or more, and more preferably 150 Pa·s or more, as well as preferably 500 Pa·s or less, and more preferably 400 Pa·s or less. When the foregoing viscosity is at or above the lower limit and at or below the upper limit, the effects of the present invention can be more effectively exhibited.

The viscosity at 25 °C of the hemocyte separation composition is measured using an E-type viscometer (For example, "TVE-35" manufactured by Toki Sangyo Co., Ltd.) under the conditions of 25 °C and a shear rate of 1.0 $sec^{-1}$.

<Hemocyte Separation Jig>

The hemocyte separation jig is a jig that moves to between leukocytes and erythrocytes during centrifugation to form a partition. In addition, the hemocyte separation jig is used for the purpose of preventing erythrocytes from contaminating in a layer of leukocytes after centrifugation.

As the hemocyte separation jig, for example, a jig known as a serum or plasma separation jig can be used. Examples of the hemocyte separation jig include a mechanical separator (hemocyte separation jig) described in WO 2010/132783 A1 and the like.

Examples of the material for the hemocyte separation jig include elastomer.

(Hemagglutinating Agent)

The leukocyte concentration separation device including the configuration A1 includes a hemagglutinating agent contained in the container main body. The blood collection container including the configuration A2 includes a hemagglutinating agent contained in the blood collection container main body. As the hemagglutinating agent, a conventionally known hemagglutinating agent can be used. One kind of the hemagglutinating agent may be used alone, or two or more kinds of the same may be used in combination.

Examples of the hemagglutinating agent include: polysaccharides such as dextran, hydroxyethyl starch, methyl cellulose, and polysucrose; cationic polymers such as polyamino acid, polyamine sulfone, polybrene, polyalkylene oxide, polyalkylene imine, polyacrylamide, and cation-modified polyvinyl alcohol; polyethylene glycol (PEG); low molecular weight compounds such as vancomycin and kanamycin; and cell-binding glycoprotein such as plant lectin.

The hemagglutinating agent is preferably a polysaccharide or polyethylene glycol, and more preferably a polysaccharide. The hemagglutinating agent is preferably dextran, hydroxyethyl starch, or polyethylene glycol, and more preferably dextran. In this case, the effects of the present invention can be more effectively exhibited. In addition, adhesion of the blood cell separation composition with the container main body or the blood collection container main body is enhanced, which makes it possible to effectively prevent erythrocytes from remaining in the gap between the hemocyte separation composition and the container main body or the blood collection container main body after centrifugation.

The above-described dextran has a weight average molecular weight of preferably 50,000 or more, more preferably 70,000 or more, and further preferably 100,000 or more, as well as preferably 1 million or less, more preferably 600,000 or less, and further preferably 300,000 or less. When the weight average molecular weight is at or above the lower limit and at or below the upper limit, the effects of the present invention can be further more effectively exhibited. In addition, adhesion of the blood cell separation composition with the container main body or the blood collection container main body is further enhanced, which makes it possible to more effectively prevent erythrocytes from remaining in the gap between the hemocyte separation composition and the container main body or the blood collection container main body after centrifugation.

The above-described hydroxyethyl starch has a weight average molecular weight of preferably 70,000 or more, more preferably 100,000 or more, and further preferably 200,000 or more, as well as preferably 1 million or less, more preferably 700,000 or less, and further preferably 500,000 or less. When the weight average molecular weight is at or above the lower limit and at or below the upper limit, the effects of the present invention can be further more effectively exhibited. In addition, adhesion of the blood cell separation composition with the container main body or the blood collection container main body is further enhanced, which makes it possible to more effectively prevent erythrocytes from remaining in the gap between the hemocyte separation composition and the container main body or the blood collection container main body after centrifugation.

The above-described polyethylene glycol has a weight average molecular weight of preferably 1,000 or more, more preferably 3,000 or more, and further preferably 5,000 or more, as well as preferably 100,000 or less, more preferably 50,000 or less, and further preferably 30,000 or less. When the weight average molecular weight is at or above the lower limit and at or below the upper limit, the effects of the present invention can be further more effectively exhibited. In addition, adhesion of the blood cell separation composition with the container main body or the blood collection container main body is further enhanced, which makes it possible to more effectively prevent erythrocytes from remaining in the gap between the hemocyte separation composition and the container main body or the blood collection container main body after centrifugation.

The weight average molecular weight refers to a weight average molecular weight in terms of pullulan measured by gel permeation chromatography (GPC).

In the leukocyte concentration separation device, the hemagglutinating agent may be contained in a state of powder or in a state of being dissolved in a liquid in the container main body. When the hemagglutinating agent is contained in a state of being dissolved in a liquid in the container main body, the osmotic pressure of the liquid is preferably adjusted to be isotonic with the blood in order to prevent hemolysis upon blood inflow. The hemagglutinating agent may be present in both states, a state of powder and a state of being dissolved in a liquid, in the container main body.

In the blood collection container, the hemagglutinating agent may be contained in a state of powder or in a state of being dissolved in a liquid in the blood collection container main body. When the hemagglutinating agent is contained in a state of being dissolved in a liquid in the blood collection container main body, the osmotic pressure of the liquid is preferably adjusted to be isotonic with the blood in order to prevent hemolysis upon blood inflow. The hemagglutinating agent may be present in both states, a state of powder and a state of being dissolved in a liquid, in the blood collection container main body.

Examples of the liquid include water and alcohol.

The hemagglutinating agent is preferably disposed on an inner wall surface of the blood collection container main body or disposed on a surface of the hemocyte separation material. The hemagglutinating agent may be disposed on the inner wall surface of the blood collection container main body, may be disposed on the surface of the hemocyte separation material, or may be disposed on both the inner wall surface of the blood collection container main body and the surface of the hemocyte separation material. In the case of the leukocyte concentration separation device as well, the hemagglutinating agent is preferably disposed on an inner wall surface of the container main body or disposed on a surface of the hemocyte separation material.

When the hemagglutinating agent is contained in a state of powder, the hemagglutinating agent in the powder state preferably adheres to an inner wall surface of the blood collection container main body or disposed on a surface of the hemocyte separation material. In the case of the leukocyte concentration separation device as well, the hemagglutinating agent in the powder state is preferably disposed on an inner wall surface of the container main body or disposed on a surface of the hemocyte separation material.

In the leukocyte concentration separation device, the content of the hemagglutinating agent is preferably 5 mg or more, and more preferably 10 mg or more, as well as preferably 50 mg or less, and more preferably 30 mg or less per 1 mL of an added blood-derived sample. In the blood collection container, the content of the hemagglutinating agent is preferably 5 mg or more, and more preferably 10 mg or more, as well as preferably 50 mg or less, and more preferably 30 mg or less per 1 mL of collected blood. When the content of the hemagglutinating agent is at or above the lower limit and at or below the upper limit, the effects of the present invention can be further more effectively exhibited. In addition, adhesion of the blood cell separation composition with the blood collection container main body is further enhanced, which makes it possible to more effectively prevent erythrocytes from remaining in the gap between the hemocyte separation composition and the blood collection container main body after centrifugation.

(Osmotic Pressure Regulator)

The leukocyte concentration separation device including the configuration B1 includes an osmotic pressure regulator contained in the container main body. The blood collection container including the configuration B2 includes an osmotic pressure regulator contained in the blood collection container main body. As the osmotic pressure regulator, a conventionally known osmotic pressure regulator can be used. One kind of the osmotic pressure regulator may be used alone, or two or more kinds of the same may be used in combination.

Examples of the osmotic pressure regulator include sodium chloride, potassium chloride, glucose, dihydroxyacetone, and sugar alcohols such as D-mannitol and D-sorbitol.

From the viewpoint of more effectively exhibiting the effects of the present invention, the osmotic pressure regulator is preferably sodium chloride or glucose.

In the leukocyte concentration separation device, the osmotic pressure regulator may be contained in a state of powder or in a state of being dissolved in a liquid in the container main body. The osmotic pressure regulator may be present in both states, a state of powder and a state of being dissolved in a liquid, in the container main body.

In the blood collection container, the osmotic pressure regulator may be contained in a state of powder or in a state of being dissolved in a liquid in the blood collection container main body. The osmotic pressure regulator may be present in both states, a state of powder and a state of being dissolved in a liquid, in the blood collection container main body.

Examples of the liquid include water and alcohol.

The osmotic pressure regulator is preferably disposed on an inner wall surface of the blood collection container main body or disposed on a surface of the hemocyte separation material. The osmotic pressure regulator may be disposed on the inner wall surface of the blood collection container main body, may be disposed on the surface of the hemocyte separation material, or may be disposed on both the inner wall surface of the blood collection container main body and the surface of the hemocyte separation material. In the case of the leukocyte concentration separation device as well, the osmotic pressure regulator is preferably disposed on an inner wall surface of the container main body or disposed on a surface of the hemocyte separation material.

When the osmotic pressure regulator is contained in a state of powder, the osmotic pressure regulator in the powder state preferably adheres to an inner wall surface of the blood collection container main body or disposed on a surface of the hemocyte separation material. In the case of the leukocyte concentration separation device as well, the osmotic pressure regulator in the powder state is preferably disposed on an inner wall surface of the container main body or disposed on a surface of the hemocyte separation material.

The amount of the osmotic pressure regulator contained in the container main body or the blood collection container main body is not particularly limited as long as the osmotic pressure of the solution for osmotic pressure measurement satisfies the above-described range.

(Anticoagulant)

The leukocyte concentration separation device preferably includes an anticoagulant contained in the container main body. The blood collection container preferably includes an anticoagulant contained in the blood collection container main body. As the anticoagulant, a conventionally known anticoagulant can be used. One kind of the anticoagulant may be used alone, or two or more kinds of the same may be used in combination.

Examples of the anticoagulant include heparin, ethylenediaminetetraacetic acid (EDTA), and citric acid.

In the leukocyte concentration separation device, the anticoagulant may be contained in a state of powder or in a state of being dissolved in a liquid in the container main body. When the anticoagulant is contained in a state of being dissolved in a liquid in the container main body, the osmotic pressure of the liquid is preferably adjusted to be isotonic with the blood in order to prevent hemolysis upon blood inflow. The anticoagulant may be present in both states, a state of powder and a state of being dissolved in a liquid, in the container main body.

In the blood collection container, the anticoagulant may be contained in a state of powder or in a state of being dissolved in a liquid in the blood collection container main body. When the anticoagulant is contained in a state of being dissolved in a liquid in the blood collection container main body, the osmotic pressure of the liquid is preferably adjusted to be isotonic with the blood in order to prevent hemolysis upon blood inflow. The anticoagulant may be present in both states, a state of powder and a state of being dissolved in a liquid, in the blood collection container main body.

Examples of the liquid include water and alcohol.

The anticoagulant is preferably disposed on an inner wall surface of the blood collection container main body or disposed on a surface of the hemocyte separation material. The anticoagulant may be disposed on the inner wall surface of the blood collection container main body, may be disposed on the surface of the hemocyte separation material, or may be disposed on both the inner wall surface of the blood collection container main body and the surface of the hemocyte separation material. In the case of the leukocyte concentration separation device as well, the anticoagulant is preferably disposed on an inner wall surface of the container main body or disposed on a surface of the hemocyte separation material.

When the anticoagulant is contained in a state of powder, the anticoagulant in the powder state preferably adheres to an inner wall surface of the blood collection container main body or disposed on a surface of the hemocyte separation material. In the case of the leukocyte concentration separation device as well, the anticoagulant in the powder state is preferably disposed on an inner wall surface of the container main body or disposed on a surface of the hemocyte separation material.

The amount of the anticoagulant contained in the container main body or the blood collection container main body is not particularly limited as long as the effects of the present invention are not impaired.

(Antioxidant)

The leukocyte concentration separation device preferably includes an antioxidant contained in the container main body. The blood collection container preferably includes an antioxidant contained in the blood collection container main body. By including the antioxidant, it is possible to effectively suppress denaturation when the leukocyte concentration separation device and the blood collection container are radiation-sterilized. As the antioxidant, a conventionally known antioxidant can be used. One kind of the antioxidant may be used alone, or two or more kinds of the same may be used in combination.

Examples of the antioxidant include ascorbic acid and inorganic salts of ascorbic acid.

In the leukocyte concentration separation device, the antioxidant may be contained in a state of powder or in a state of being dissolved in a liquid in the container main body. When the antioxidant is contained in a state of being dissolved in a liquid in the container main body, the osmotic pressure of the liquid is preferably adjusted to be isotonic with the blood in order to prevent hemolysis upon blood inflow. The antioxidant may be present in both states, a state of powder and a state of being dissolved in a liquid, in the container main body.

In the blood collection container, the antioxidant may be contained in a state of powder or in a state of being dissolved in a liquid in the blood collection container main body. When the antioxidant is contained in a state of being dissolved in a liquid in the blood collection container main body, the osmotic pressure of the liquid is preferably adjusted to be isotonic with the blood in order to prevent hemolysis upon blood inflow. The antioxidant may be present in both states, a state of powder and a state of being dissolved in a liquid, in the blood collection container main body.

Examples of the liquid include water and alcohol.

The antioxidant is preferably disposed on an inner wall surface of the blood collection container main body or disposed on a surface of the hemocyte separation material. The antioxidant may be disposed on the inner wall surface of the blood collection container main body, may be disposed on the surface of the hemocyte separation material, or may be disposed on both the inner wall surface of the blood collection container main body and the surface of the hemocyte separation material. In the case of the leukocyte concentration separation device as well, the antioxidant is preferably disposed on an inner wall surface of the container main body or disposed on a surface of the hemocyte separation material.

When the antioxidant is contained in a state of powder, the antioxidant in the powder state preferably adheres to an inner wall surface of the blood collection container main body or disposed on a surface of the hemocyte separation material. In the case of the leukocyte concentration separation device as well, the antioxidant in the powder state is preferably disposed on an inner wall surface of the container main body or disposed on a surface of the hemocyte separation material.

The amount of the antioxidant contained in the container main body or the blood collection container main body is not particularly limited as long as the effects of the present invention are not impaired.

(Container Main Body and Blood Collection Container Main Body)

The shapes of the container main body and the blood collection container main body are not particularly limited, but are preferably bottomed tubular containers.

The materials for the container main body and the blood collection container main body are not particularly limited. Examples of the material for the container main body and the blood collection container main body include thermoplastic resins such as polyethylene, polypropylene, polystyrene, polyethylene terephthalate, polymethyl methacrylate, and polyacrylonitrile; thermosetting resins such as unsaturated polyester resins, epoxy resins, and epoxy-acrylate resins; modified natural resins such as cellulose acetate, cellulose propionate, ethyl cellulose, and ethyl chitin; silicate glasses such as soda lime glass, phosphosilicate glass, and borosilicate glass; and glasses such as quartz glass. As the material for the container main body and the blood collection container main body, one kind may be used alone, or two or more kinds may be used in combination.

(Plug)

The leukocyte concentration separation device and the blood collection container preferably include a plug. As the plug, a conventionally known plug can be used. The plug is preferably formed of a such material in such a shape that the plug can be airtightly and liquid-tightly attached to the opening of the container main body or the opening of the blood collection container main body. The plug is preferably configured such that a blood sampling needle can be inserted therethrough.

Examples of the plug include a plug having a shape fitted to the opening of the container main body or the opening of the blood collection container main body, a sheet-like seal plug, and the like.

The plug may include a plug main body such as a rubber plug and a cap member made of plastic or the like. In this case, it is possible to suppress the risk that the blood comes into contact with a human body when the plug is pulled out from the opening of the blood collection container main body after the blood collection.

Examples of the material for the plug (or the plug main body) include synthetic resins, elastomers, rubbers, and metal foils. Examples of the rubber include butyl rubber and halogenated butyl rubber. Examples of the metal foil include an aluminum foil. From the viewpoint of enhancing the sealing property, the material for the plug is preferably butyl rubber. The plug is preferably a butyl rubber plug.

(Other Details of Blood Collection Container)

The blood collection container is preferably a blood collection tube. The blood collection container main body is preferably a blood collection tube main body.

The blood collection container (blood collection container including the configuration A2 and the configuration B2) in which the hemagglutinating agent and the osmotic pressure regulator are contained in a state of being dissolved in a liquid can be manufactured, for example, as follows.

The hemagglutinating agent, the osmotic pressure regulator, and other components to be used as necessary are dissolved in a solvent such as water to obtain a mixture solution. The resulting mixture solution is added into the blood collection container main body. In addition, before or after the mixture solution is added, the hemocyte separation composition is contained in the blood collection container main body.

By volatilizing the solvent in the mixture solution or adding the hemagglutinating agent, the osmotic pressure regulator, and the like in a state of powder onto the surface of the hemocyte separation composition, the blood collection container in which the hemagglutinating agent and the osmotic pressure regulator are disposed in a state of powder on the surface of the hemocyte separation composition can be obtained.

The blood collection container (blood collection container including the configuration A2 and the configuration B2) in which the hemagglutinating agent and the osmotic pressure regulator are disposed in a state of powder on an inner wall surface of the blood collection container main body can be manufactured, for example, as follows.

The hemagglutinating agent, the osmotic pressure regulator, and other components to be used as necessary are dissolved in a solvent such as water to obtain a mixture solution. The mixture solution is applied to the inner wall surface of the blood collection container main body and dried. In addition, before or after the mixture solution is applied, the hemocyte separation composition is contained in the blood collection container main body.

In the blood collection container, the hemagglutinating agent may be contained in a state of being dissolved in a liquid, and the osmotic pressure regulator may be contained in a state of powder. In the blood collection container, for example, the hemagglutinating agent may be contained in a state of powder, and the osmotic pressure regulator may be contained in a state of being dissolved in a liquid.

In addition, the blood collection container including the configuration A2 and the blood collection container including the configuration B2 can be manufactured by using or not using the hemagglutinating agent and the osmotic pressure regulator.

FIG. 1 is a front cross-sectional view of a blood collection container according to a first embodiment of the present invention.

A blood collection container 1 shown in FIG. 1 includes a blood collection container main body 2, a hemocyte separation composition 3, a mixture solution 4 containing a hemagglutinating agent, an osmotic pressure regulator, and water, as well as a plug 5. The blood collection container main body 2 has an opening at one end thereof and a closed bottom at the other end thereof. The hemocyte separation composition 3 is contained in a bottom portion of the blood collection container main body 2. The plug 5 is inserted into the opening of the blood collection container main body 2.

The mixture solution 4 is disposed on a surface of the hemocyte separation composition 3, and more specifically, on a top surface (a surface on one end side) of the hemocyte separation composition 3. The mixture solution 4 is disposed on a surface of the hemocyte separation composition 3 when the blood collection container is in an upright state. The hemagglutinating agent and the osmotic pressure regulator are contained in a state of being dissolved in a liquid in the blood collection container main body 2.

FIG. 2 is a front cross-sectional view of a blood collection container according to a second embodiment of the present invention.

A blood collection container 1A shown in FIG. 2 includes a blood collection container main body 2, a hemocyte separation composition 3, a mixture powder 4A containing a hemagglutinating agent and an osmotic pressure regulator, as well as a plug 5. The blood collection container main body 2 has an opening at one end thereof and a closed bottom at the other end thereof. The hemocyte separation composition 3 is contained in a bottom portion of the blood collection container main body 2. The plug 5 is inserted into the opening of the blood collection container main body 2.

The mixture powder 4A is disposed on an inner wall surface 2*a* of the blood collection container main body. The mixture powder 4A adheres to the inner wall surface 2*a* of the blood collection container main body. In other words, the hemagglutinating agent and the osmotic pressure regulator adhere to the inner wall surface 2*a* of the blood collection container main body. The hemagglutinating agent and the osmotic pressure regulator are contained in a state of powder in the blood collection container main body 2. The mixture powder 4A is disposed closer to one end than the hemocyte separation composition 3.

In the blood collection container according to the present invention, the hemocyte separation composition may be disposed on an inner wall surface of the blood collection container main body, and the mixture solution may be disposed in a bottom portion in the blood collection container main body when the blood collection container is in an upright state. In addition, in the blood collection container according to the present invention, the hemocyte separation composition may be disposed on an inner wall surface of the blood collection container main body, and the mixture powder may be disposed on the inner wall surface of the blood collection container main body or on a surface of the hemocyte separation composition. In the blood collection container according to the present invention, the hemocyte separation composition may be disposed on an inner wall surface of the blood collection container main body, and the mixture powder may be disposed in a bottom portion in the blood collection container main body. In addition, the hemocyte separation jig may be used instead of the hemocyte separation composition.

The leukocyte concentration separation device and the blood collection container have an internal pressure that is not particularly limited. The blood collection container can be used as a vacuum blood collection tube that is sealed by the hermetic member after the inside is evacuated. When the blood collection container is a vacuum blood collection tube, it is possible to easily collect a certain amount of blood regardless of the technical difference of the blood collector.

From the viewpoint of preventing bacterial infection, the inside of leukocyte concentration separation device and the blood collection container is preferably sterilized in accordance with the standards of ISO and JIS.

(Method for Separating Leukocytes)

The method for separating leukocytes according to the present invention is a method for separating leukocytes using the above-described blood collection container, the method including the steps of: collecting blood in the blood collection container; and centrifuging the blood collection container by which the blood has been collected. The method for separating leukocytes is a method for separating leukocytes from blood. The method for separating leukocytes is a method for concentrating and separating leukocytes from blood.

In addition, leukocytes can be separated in the same manner using the leukocyte concentration separation device. The method for separating leukocytes includes the steps of: adding a blood-derived sample into the leukocyte concentration separation device; and centrifuging the leukocyte concentration separation device into which the blood-derived sample has been added.

In the centrifugation step, a partition made of a hemocyte separation material can be formed between leukocytes and erythrocytes. After centrifugation, leukocytes can be concentrated and separated on the partition formed by the hemocyte separation material. After centrifugation, leukocytes are preferably deposited on the partition. The leukocytes concentrated and separated on the partition can be recovered as a specimen.

The centrifugation conditions in the centrifugation step are not particularly limited as long as a partition is formed with the hemocyte separation material to separate leukocytes and erythrocytes. Examples of the centrifugation conditions include a condition of performing centrifugation at 400 G or more and 4000 G or less for 10 minutes or more and 120 minutes or less.

(Leukocyte Separation System)

The leukocyte concentration separation system according to the present invention is a leukocyte concentration separation system in which predetermined amount of a blood-derived sample is collected, the leukocyte concentration separation system being intended to concentrate and separate leukocytes present in the blood-derived sample, the leukocyte concentration separation system including a hemocyte separation material having a specific gravity at 25 °C of 1.075 or more and 1.093 or less, and the leukocyte concentration separation system including a configuration A3 or a configuration B3 below.

A configuration A3: the leukocyte concentration separation system including a hemagglutinating agent.

A configuration B3: the leukocyte concentration separation system including an osmotic pressure regulator, and when a water-soluble component to be mixed with the blood-derived sample is dissolved with physiological saline in an amount equal to the predetermined amount of the blood-derived sample to obtain a solution for osmotic pressure measurement, the solution for osmotic pressure measurement having an osmotic pressure of 300 mOsm/L or more and 500 mOsm/L or less.

The leukocyte separation system according to the present invention, having the above-described configuration, is capable of obtaining a specimen with a high leukocyte recovery rate and a small amount of contaminating erythrocytes.

The leukocyte concentration separation system according to the present invention may include the configuration A3, or may include the configuration B3, or may include both of the configurations A3 and B3. From the viewpoint of more effectively exhibiting the effects of the present invention, the leukocyte concentration separation system according to the present invention preferably includes the configuration A3 and the configuration B3.

Examples of the water-soluble component to be mixed with the blood-derived sample in the configuration B3 include an osmotic pressure regulator, a hemagglutinating agent, and a liquid containing them.

In the leukocyte concentration separation system, preferred configurations and the like of the hemagglutinating agent, the osmotic pressure regulator, and the solution for osmotic pressure measurement are the same as those described above.

The leukocyte concentration separation system preferably includes a storage section that stores a blood-derived sample. It is preferable that the hemocyte separation material, the hemagglutinating agent, and the osmotic pressure regulator are provided in the storage section, but the present invention is not limited thereto.

Hereinafter, the present invention is described in more detail with reference to Examples. The present invention is not limited only to the following examples.

The following materials were prepared as materials for hemocyte separation composition.

(Materials of Organic Component Having Fluidity at 25 °C)

(Meth)Acrylic Resin:

(Meth)acrylic acid ester-based resin having fluidity at 25 °C was obtained by radical-polymerizing 2-ethylhexyl acrylate and butyl acrylate in the presence of an azo-based polymerization initiator by a solution polymerization method.

Other Resins:

Petroleum resin ("Regalite S5090" manufactured by Eastman Chemical Company)

Dicyclopentadiene resin 1 ("SCOREZ SU-500" manufactured by KOLON Industries, Inc.)

Dicyclopentadiene resin 2 ("SCOREZ SU-90" manufactured by KOLON Industries, Inc.)

Organic Compound:

Trimellitic acid ester (benzene polycarboxylic acid alkyl ester derivative, "Monocizer W-700" manufactured by DIC Corporation)

(Inorganic Fine Powder)

Hydrophilic silica (fine powder silica, "200CF" manufactured by Nippon Aerosil Co., Ltd.)

Hydrophobic silica (fine powder silica, "R974" manufactured by Nippon Aerosil Co., Ltd.)

Titanium oxide powder ("A-100" manufactured by Ishihara Sangyo Kaisha, Ltd.)

(Other Components)

Silicone oil ("SF8410" manufactured by Toray Dow Corning, Co., Ltd.)

Organic gelling agent ("Gelall D" manufactured by New Japan Chemical Co., Ltd.)

1-methyl-2-pyrrolidone (auxiliary solvent)

Preparation of Hemocyte Separation Compositions A to H:

Hemocyte separation compositions A to H having thixotropy were produced by mixing an organic component having fluidity at 25 °C, an inorganic fine powder, and other components at blending ratios shown in Tables 1 and 2.

TABLE 1

| | | | | Hemocyte separation composition A | Hemocyte separation composition B | Hemocyte separation composition C | Hemocyte separation composition D |
|---|---|---|---|---|---|---|---|
| Organic component having fluidity at 25° C. | (Meth)acrylic resin | | wt % | 94.60 | 93.50 | 93.10 | 92.70 |
| | Petroleum resin | | wt % | — | — | — | — |
| | Dicyclopentadiene resin 1 | | wt % | — | — | — | — |
| | Dicyclopentadiene resin 2 | | wt % | — | — | — | — |
| | Trimellitic acid ester | | wt % | — | — | — | — |
| Inorganic fine powder | Fine powder silica | Hydrophilic silica | wt % | 0.75 | 0.75 | 0.60 | 0.60 |
| | | Hydrophobic silica | wt % | 2.45 | 2.45 | 2.60 | 2.60 |
| | Titanium oxide powder | | wt % | 2.10 | 3.20 | 3.60 | 4.00 |
| Others | Silicone oil | | wt % | 0.10 | 0.10 | 0.10 | 0.10 |
| | Organic gelling agent | | wt % | — | — | — | — |
| | 1-Methyl-2-pyrrolidone | | wt % | — | — | — | — |
| Total | | | wt % | 100.00 | 100.00 | 100.00 | 100.00 |

TABLE 2

| | | | Hemocyte separation composition E | Hemocyte separation composition F | Hemocyte separation composition G | Hemocyte separation composition H |
|---|---|---|---|---|---|---|
| Organic component having fluidity at 25° C. | (Meth)acrylic resin | wt % | — | 92.40 | 92.00 | 91.60 |
| | Petroleum resin | wt % | 13.75 | — | — | — |
| | Dicyclopentadiene resin 1 | wt % | 17.09 | — | — | — |
| | Dicyclopentadiene resin 2 | wt % | 18.71 | — | — | — |
| | Trimellitic acid ester | wt % | 42.39 | — | — | — |
| Inorganic fine powder | Fine powder silica Hydrophilic silica | wt % | 0.71 | 0.60 | 0.40 | 0.30 |
| | Fine powder silica Hydrophobic silica | wt % | 1.79 | 2.60 | 2.50 | 3.00 |
| | Titanium oxide powder | wt % | 5.20 | 4.30 | 5.00 | 5.00 |
| Others | Silicone oil | wt % | — | 0.10 | 0.10 | 0.10 |
| | Organic gelling agent | wt % | 0.06 | — | — | — |
| | 1-Methyl-2-pyrrolidone | wt % | 0.30 | — | — | — |
| Total | | wt % | 100.00 | 100.00 | 100.00 | 100.00 |

(Hemagglutinating Agent)

Dextran (weight average molecular weight 200,000)

Hydroxyethyl starch-containing liquid ("HES 40" manufactured by NIPRO Corporation, an aqueous solution containing hydroxyethyl starch having a weight average molecular weight of about 400,000 at a concentration of 6 w/v %)

Polyethylene glycol (PEG 6K, manufactured by FUJIFILM Wako Pure Chemical Corporation)

(Osmotic Pressure Regulator)

Sodium chloride

Glucose (Anticoagulant)

Ethylenediaminetetraacetic acid dipotassium salt dihydrate (EDTA-2K.2$H_2O$)

(Antioxidant)

Sodium ascorbate

Example 1

The hemagglutinating agent, the osmotic pressure regulator, and the anticoagulant were dissolved in water to obtain a mixture solution. The types and blending amounts of the blending components of the obtained mixture solutions are shown in Table 3. The osmotic pressure of the obtained mixture solution was adjusted to be isotonic with blood.

A 100 mm-long bottomed tube made of polyethylene terephthalate (PET bottomed tube, blood collection container main body), with an opening having an inner diameter of 14 mm, was prepared. A hemocyte separation composition B of 2.0 g was contained in a bottom portion of the blood collection container main body. In addition, 1.0 mL of the obtained mixture solution was added onto the surface of the hemocyte separation composition B. The inside of the blood collection container was depressurized and sealed with a butyl rubber stopper. In this way, a blood collection container was produced. In the obtained blood collection container, the hemagglutinating agent, the osmotic pressure regulator, and the anticoagulant were disposed on the surface of the hemocyte separation composition in a state of being dissolved in a liquid. The obtained blood collection container was a container for collecting 4 mL of blood.

Examples 2 to 16 and Comparative Examples 3 and 5

Blood collection containers were prepared in the same manner as in Example 1 except that the type of the hemocyte separation composition and the blending amounts of the hemagglutinating agent, the anticoagulant, the antioxidant, and the osmotic pressure regulator were changed as shown in Tables 3 to 7. In the tables, the blending amount of the hydroxyethyl starch-containing liquid was indicated not by the content of hydroxyethyl starch but by the blending amount of the hydroxyethyl starch-containing liquid (commercially available product). The osmotic pressure of the obtained mixture solution was adjusted to be isotonic or hypertonic with blood.

Comparative Example 1

The anticoagulant was dissolved in water to obtain a mixture solution.

A 100 mm-long PET bottomed tube (blood collection container main body), with an opening having an inner diameter of 14 mm, was prepared. A hemocyte separation composition D of 2.0 g was contained in a bottom portion of the blood collection container main body. In addition, 30 mg of the obtained mixture solution was applied to the inner wall surface of the blood collection container main body and was dried. The inside of the blood collection container was depressurized and sealed with a butyl rubber stopper. In this way, a blood collection container was produced. The obtained blood collection container was a container for collecting 4 mL of blood.

Comparative Examples 2 and 4

Blood collection containers were produced in the same manner as in Comparative Example 1 except that the type of the hemocyte separation composition was changed as shown in Table 7.

(Evaluation)

(1) Specific Gravity of Hemocyte Separation Composition at 25 °C.

Drops of the hemocyte separation composition were dropped one by one sequentially into saline at 25 °C whose specific gravity was adjusted stepwise at intervals of 0.002, and the specific gravity was determined based on rise and fall of each drop in saline.

(2) Osmotic Pressure of Solution for Osmotic Pressure Measurement

To the obtained blood collection container, 4 mL of physiological saline was added. After the addition, the resultant was mixed by inversion so that the water-soluble component was dissolved with physiological saline, whereby a solution for osmotic pressure measurement was obtained. The osmotic pressure of the obtained solution for osmotic pressure measurement was measured by the freezing point depressing method using an osmosis meter ("OM-6060" manufactured by ARKRAY Inc.).

(3) Erythrocyte Contamination Rate and Leukocyte Recovery Rate

The blood of three persons was prepared, and the following steps were sequentially performed.

Blood Collection Step:

In the blood collection container main body of the obtained blood collection container, 4 mL of blood was collected.

Centrifugation Step:

The blood collection container was centrifuged at 1500 G for 15 minutes.

After centrifugation, plasma was located above a partition formed with the hemocyte separation composition. The plasma was stirred by pipetting so that hemocytes deposited on the partition formed with the hemocyte separation composition were suspended, and then the hemocytes were recovered as a specimen.

The recovered specimen was analyzed using a multi-item automatic hemocyte analyzer ("XE5000" manufactured by Sysmex Corporation) to count the number of leukocytes and the number of erythrocyte in the specimen. In addition, for the prepared blood (whole blood sample), the number of leukocytes and the number of erythrocytes in the whole blood sample were measured in the same manner. The number of leukocytes and the number of erythrocytes were average values of results obtained by evaluating the prepared blood of the three persons.

The erythrocyte contamination rate and the leukocyte recovery rate were calculated by the following formula.

Erythrocyte contamination rate (%)=(Number (cells) of erythrocytes contained in recovered specimen)/(Number (cells) of erythrocytes contained in whole blood sample)×100

Leukocyte recovery rate (%)=(Number (cells) of leukocytes contained in recovered specimen)/(Number (cells) of leukocytes contained in whole blood sample)×100

[Criteria for Erythrocyte Contamination Rate]

○: Erythrocyte contamination rate is 2% or less x: Erythrocyte contamination rate is more than 2%.

[Criteria for Leukocyte Recovery Rate]

○: Leukocyte recovery rate is 40% or more.

x: Leukocyte recovery rate is less than 40%.

The compositions and the results are shown in Tables 3 to 7.

TABLE 3

| | | | | Example 1 | Example 2 | Example 3 | Example 4 |
|---|---|---|---|---|---|---|---|
| Mixture solution | Hemagglutinating agent | Dextran | wt % | 6.00 | 6.00 | 6.00 | — |
| | | Hydroxyethyl starch-containing liquid | wt % | — | — | — | 99.22 |
| | | PEG 6K | wt % | — | — | — | — |
| | Osmotic pressure regulator | NaCl | wt % | 0.70 | 0.70 | 0.70 | — |
| | | Glucose | wt % | — | — | — | — |
| | Anticoagulant | EDTA 2K•2$H_2O$ | wt % | 0.78 | 0.78 | 0.78 | 0.78 |
| | Antioxidant | Sodium ascorbate | wt % | — | — | — | — |
| | Solvent | Water | wt % | 92.52 | 92.52 | 92.52 | — |
| | Total | | wt % | 100 | 100 | 100 | 100 |
| Evaluation | Hemocyte separation composition | Type | — | B | D | G | D |
| | | Specific gravity at 25° C. | — | 1.077 | 1.085 | 1.092 | 1.085 |
| | Osmotic pressure of solution for osmotic pressure measurement | | mOsm/L | 290 | 290 | 290 | 295 |
| | Erythrocyte contamination rate | | % | 1.2 | 1.3 | 1.5 | 1.2 |
| | | | Determination | ○ | ○ | ○ | ○ |
| | Leukocyte recovery rate | | % | 45 | 92 | 95 | 88 |
| | | | Determination | ○ | ○ | ○ | ○ |

TABLE 4

| | | | | Example 5 | Example 6 | Example 7 | Example 8 |
|---|---|---|---|---|---|---|---|
| Mixture solution | Hemagglutinating agent | Dextran | wt % | — | — | — | — |
| | | Hydroxyethyl starch-containing liquid | wt % | — | — | — | — |
| | | PEG 6K | wt % | 8.00 | — | — | — |
| | Osmotic pressure regulator | NaCl | wt % | 0.70 | 1.02 | 1.15 | 1.48 |
| | | Glucose | wt % | — | — | — | — |
| | Anticoagulant | EDTA 2K•2$H_2O$ | wt % | 0.78 | 0.78 | 0.78 | 0.78 |
| | Antioxidant | Sodium ascorbate | wt % | — | — | — | — |
| | Solvent | Water | wt % | 90.52 | 98.20 | 98.07 | 97.74 |
| | Total | | wt % | 100 | 100 | 100 | 100 |
| Evaluation | Hemocyte separation composition | Type | — | D | D | D | D |
| | | Specific gravity at 25° C. | — | 1.085 | 1.085 | 1.085 | 1.085 |

TABLE 4-continued

| | | | Example 5 | Example 6 | Example 7 | Example 8 |
|---|---|---|---|---|---|---|
| | Osmotic pressure of solution for osmotic pressure measurement | mOsm/L | 291 | 304 | 312 | 334 |
| | Erythrocyte contamination rate | % | 1.3 | 1.9 | 1.6 | 1 |
| | | Determination | ○ | ○ | ○ | ○ |
| | Leukocyte recovery rate | % | 90 | 77 | 75 | 66 |
| | | Determination | ○ | ○ | ○ | ○ |

TABLE 5

| | | | | Example 9 | Example 10 | Example 11 | Example 12 |
|---|---|---|---|---|---|---|---|
| Mixture solution | Hemagglutinating agent | Dextran | wt % | 6.00 | 6.00 | 6.00 | 6.00 |
| | | Hydroxyethyl starch-containing liquid | wt % | — | — | — | — |
| | | PEG 6K | wt % | — | — | — | — |
| | Osmotic pressure regulator | NaCl | wt % | 1.70 | 1.32 | 1.40 | 1.30 |
| | | Glucose | wt % | — | — | — | — |
| | Anticoagulant | EDTA 2K•2$H_2$0 | wt % | 0.78 | 0.78 | 0.78 | 0.78 |
| | Antioxidant | Sodium ascorbate | wt % | — | — | — | 1.20 |
| | Solvent | Water | wt % | 91.52 | 91.90 | 91.82 | 90.72 |
| | Total | | wt % | 100 | 100 | 100 | 100 |
| Evaluation | Hemocyte separation composition | Type | — | C | D | D | D |
| | | Specific gravity at 25° C. | — | 1.082 | 1.085 | 1.085 | 1.085 |
| | Osmotic pressure of solution for osmotic pressure measurement | | mOsm/L | 348 | 324 | 330 | 348 |
| | Erythrocyte contamination rate | | % | 0.7 | 0.9 | 0.6 | 0.6 |
| | | | Determination | ○ | ○ | ○ | ○ |
| | Leukocyte recovery rate | | % | 63 | 70 | 65 | 68 |
| | | | Determination | ○ | ○ | ○ | ○ |

TABLE 6

| | | | | Example 13 | Example 14 | Example 15 | Example 16 |
|---|---|---|---|---|---|---|---|
| Mixture solution | Hemagglutinating agent | Dextran | wt % | — | — | 6.00 | 6.00 |
| | | Hydroxyethyl starch-containing liquid | wt % | 98.42 | — | — | — |
| | | PEG 6K | wt % | — | 8.00 | — | — |
| | Osmotic pressure regulator | NaCl | wt % | 0.80 | 0.50 | — | 2.00 |
| | | Glucose | wt % | — | — | 5.00 | — |
| | Anticoagulant | EDTA 2K•2$H_2$0 | wt % | 0.78 | 0.78 | 0.78 | 0.78 |
| | Antioxidant | Sodium ascorbate | wt % | — | — | — | — |
| | Solvent | Water | wt % | — | 90.72 | 88.22 | 91.22 |
| | Total | | wt % | 100 | 100 | 100 | 100 |
| Evaluation | Hemocyte separation composition | Type | — | C | D | F | E |
| | | Specific gravity at 25° C. | — | 1.082 | 1.085 | 1.087 | 1.085 |
| | Osmotic pressure of solution for osmotic pressure measurement | | mOsm/L | 350 | 331 | 330 | 368 |
| | Erythrocyte contamination rate | | % | 0.7 | 0.5 | 0.7 | 0.5 |
| | | | Determination | ○ | ○ | ○ | ○ |
| | Leukocyte recovery rate | | % | 62 | 66 | 62 | 48 |
| | | | Determination | ○ | ○ | ○ | ○ |

TABLE 7

| | | | | Comparative Example 1 | Comparative Example 2 | Comparative Example 3 | Comparative Example 4 | Comparative Example 5 |
|---|---|---|---|---|---|---|---|---|
| Mixture solution | Hemagglutinating agent | Dextran | wt % | — | — | 6.00 | — | — |
| | | Hydroxyethyl starch-containing liquid | wt % | — | — | — | — | — |
| | | PEG 6K | wt % | — | — | — | — | — |
| | Osmotic pressure regulator | NaCl | wt % | — | — | 0.70 | — | 5.30 |
| | | Glucose | wt % | — | — | — | — | — |
| | Anticoagulant | EDTA 2K•2$H_2$0 | wt % | 26 | 26 | 0.78 | 26 | 0.78 |
| | Antioxidant | Sodium ascorbate | wt % | — | — | — | — | — |
| | Solvent | Water | wt % | 74.00 | 74.00 | 92.52 | 74.00 | 93.92 |
| | Total | | wt % | 100 | 100 | 100 | 100 | 100 |

TABLE 7-continued

| | | | | Comparative Example 1 | Comparative Example 2 | Comparative Example 3 | Comparative Example 4 | Comparative Example 5 |
|---|---|---|---|---|---|---|---|---|
| Evaluation | Hemocyte separation composition | Type | — | D | B | H | A | G |
| | | Specific gravity at 25° C. | — | 1.085 | 1.077 | 1.095 | 1.070 | 1.092 |
| | Osmotic pressure of solution for osmotic pressure measurement | | mOsm/L | 290 | 290 | 290 | 290 | 578 |
| | Erythrocyte contamination rate | | % | 3 | 2.6 | 4.6 | 0.3 | 1.2 |
| | | | Determination | X | X | X | ○ | ○ |
| | Leukocyte recovery rate | | % | 95 | 45 | 96 | 25 | 28 |
| | | | Determination | ○ | ○ | ○ | X | X |

EXPLANATION OF SYMBOLS

1, 1A: Blood collection container
2: Blood collection container main body
2*a*: Inner wall surface
3: Hemocyte separation composition
4: Mixture solution
4A: Mixture powder
5: Plug

The invention claimed is:

1. A leukocyte concentration separation device into which a predetermined amount of a blood-derived sample is added, the leukocyte concentration separation device being intended to concentrate and separate leukocytes present in the blood-derived sample, the leukocyte concentration separation device comprising: a container main body; and a hemocyte separation material contained in the container main body, the hemocyte separation material having a specific gravity at 25 °C of 1.082 or more and 1.090 or less, and the leukocyte concentration separation device including a configuration A1 and a configuration B1 below: a configuration A1: the leukocyte concentration separation device including a hemagglutinating agent contained in the container main body; a configuration B1: the leukocyte concentration separation device including an osmotic pressure regulator contained in the container main body, and when a water-soluble component contained in the container main body is dissolved with physiological saline in an amount equal to the predetermined amount of a blood-derived sample to be added into the leukocyte concentration separation device to obtain a solution for osmotic pressure measurement, the solution for osmotic pressure measurement having an osmotic pressure of 320 mOsm/L or more and 360 mOsm/L or less.

2. A blood collection container by which a predetermined amount of blood is collected, the blood collection container comprising:

a blood collection container main body; and a hemocyte separation material contained in the blood collection container main body, the hemocyte separation material having a specific gravity at 25 °C of 1.082 or more and 1.090 or less, and the blood collection container including a configuration A2 and a configuration B2 below:

a configuration A2: the blood collection container including a hemagglutinating agent contained in the blood collection container main body;

a configuration B2: the blood collection container including an osmotic pressure regulator contained in the blood collection container main body, and when a water-soluble component contained in the blood collection container main body is dissolved with physiological saline in an amount equal to the predetermined amount of blood to be collected in the blood collection container to obtain a solution for osmotic pressure measurement, the solution for osmotic pressure measurement having an osmotic pressure of 320 mOsm/L or more and 360 mOsm/L or less.

3. The blood collection container according to claim 2, wherein the hemocyte separation material is a hemocyte separation composition having thixotropy.

4. The blood collection container according to claim 2, wherein the hemagglutinating agent is dextran, hydroxyethyl starch, or polyethylene glycol.

5. The blood collection container according to claim 4, wherein the dextran has a weight average molecular weight of 50,000 or more.

6. The blood collection container according to claim 2, wherein the osmotic pressure regulator is sodium chloride or glucose.

7. The blood collection container according to claim 2, comprising an anticoagulant contained in the blood collection container main body.

8. The blood collection container according to claim 2, comprising an antioxidant contained in the blood collection container main body.

9. The blood collection container according to claim 8, wherein the antioxidant is ascorbic acid or an inorganic salt of ascorbic acid.

10. A method for separating leukocytes using the leukocyte concentration separation device according to claim 1, the method comprising the steps of:

adding a blood-derived sample into the leukocyte concentration separation device; and centrifuging the leukocyte concentration separation device into which the blood-derived sample has been added.

11. A method for separating leukocytes using the blood collection container according to claim 2, the method comprising the steps of:

collecting blood in the blood collection container; and centrifuging the blood collection container by which the blood has been collected.

12. A leukocyte concentration separation system in which a predetermined amount of a blood-derived sample is collected, the leukocyte concentration separation system being intended to concentrate and separate leukocytes present in the blood-derived sample, the leukocyte concentration separation system comprising a hemocyte separation material having a specific gravity at 25 °C of 1.082 or more and 1.090 or less, and the leukocyte concentration separation system including a configuration A3 and a configuration B3 below: a configuration A3: the leukocyte concentration separation system including a hemagglutinating agent; a configuration B3: the leukocyte concentration separation system including an osmotic pressure regulator, and when a water-soluble component to be mixed with the blood-derived sample is dissolved with physiological saline in an amount equal to the predetermined amount of the blood-derived sample to obtain a solution for osmotic pressure measurement, the solution for osmotic pressure measurement having an osmotic pressure of 320 mOsm/L or more and 360 mOsm/L or less.

* * * * *